United States Patent [19]
Garris

[11] 3,969,227
[45] July 13, 1976

[54] PHOTOELECTRIC INSPECTION OF TRANSPARENT OR TRANSLUCENT MEDICINAL CAPSULES

[75] Inventor: Charles R. Garris, Stratford, N.J.

[73] Assignee: SmithKline Corporation, Philadelphia, Pa.

[22] Filed: Nov. 1, 1974

[21] Appl. No.: 519,838

[52] U.S. Cl. .............................. 209/73; 209/74 M; 209/111.7 T; 250/577; 356/240
[51] Int. Cl.² ........................................... B07C 5/10
[58] Field of Search ............... 209/74 R; 74 M, 73, 209/75, 111.7, 111.6; 356/239, 240; 250/577, 578, 223

[56] References Cited
UNITED STATES PATENTS

| | | | |
|---|---|---|---|
| 2,905,318 | 9/1959 | Schell | 209/111.7 |
| 3,094,213 | 6/1963 | Wyman | 209/111.7 |
| 3,160,277 | 12/1964 | Wyman | 209/72 |
| 3,218,463 | 11/1965 | Calhoun | 250/223 B X |
| 3,265,901 | 8/1966 | Schneider | 209/111.7 X |
| 3,565,249 | 2/1971 | Codding | 209/74 M |
| 3,677,437 | 7/1972 | Haigler | 221/7 |
| 3,756,402 | 9/1973 | Wagers et al. | 209/111.7 X |

Primary Examiner—Robert B. Reeves
Assistant Examiner—Joseph J. Rolla
Attorney, Agent, or Firm—Smith, Harding, Earley & Follmer

[57] ABSTRACT

In a capsule filling machine, capsules held pneumatically against the periphery of a transporting disc are photoelectrically inspected by two light beams, both oblique with respect to the disc axis. Electrical gating and delay circuitry effects pneumatic removal of capsules from the disc at a location remote from the inspection location if either beam is not broken by the capsule contents.

3 Claims, 11 Drawing Figures

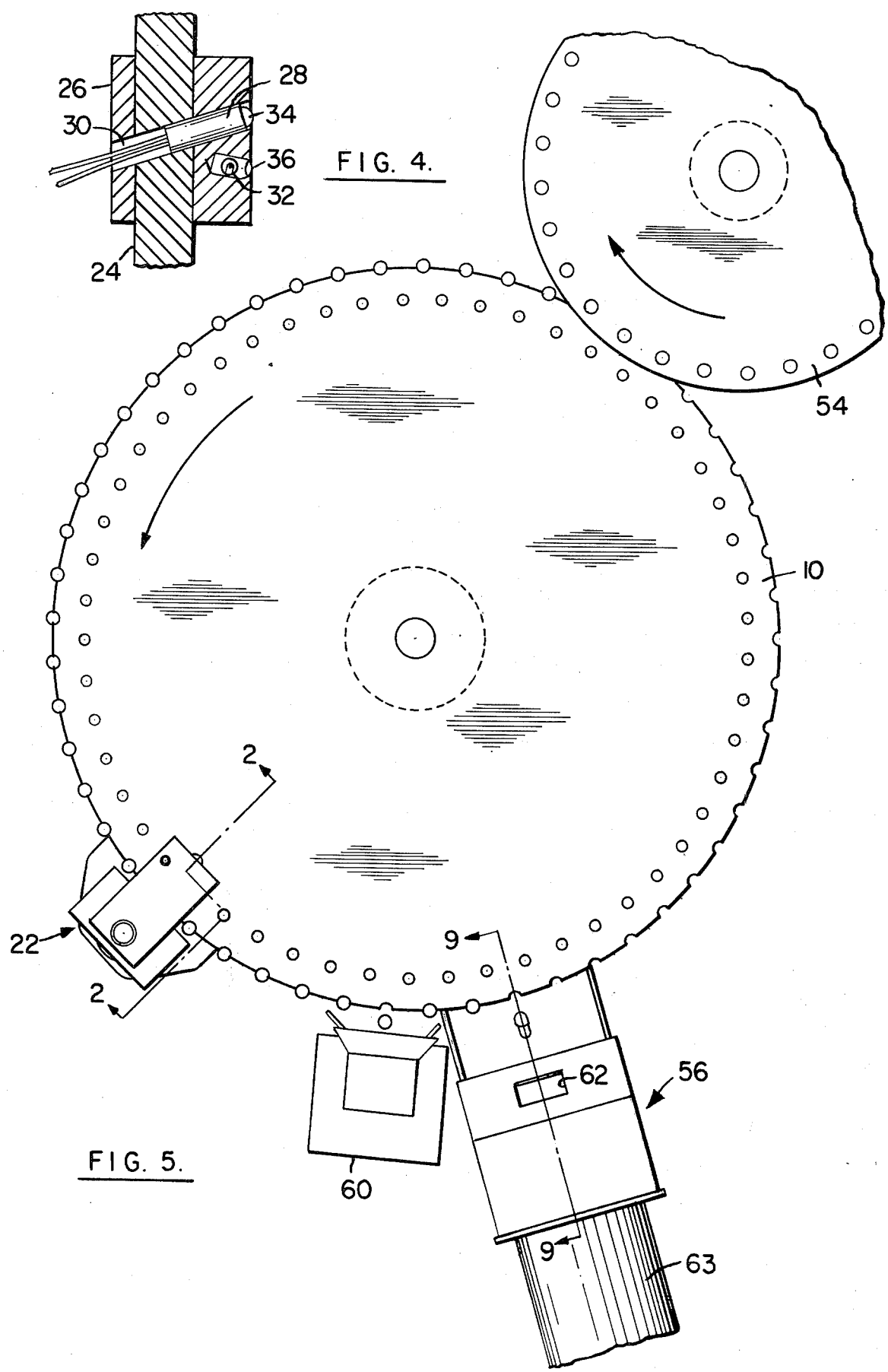

PHOTOELECTRIC INSPECTION OF TRANSPARENT OR TRANSLUCENT MEDICINAL CAPSULES

BRIEF SUMMARY OF THE INVENTION

This invention relates to photoelectric inspection, and particularly to a photoelectric inspection apparatus adapted for use in conjunction with capsule filling machinery.

In a typical capsule-filling machine, capsules are carried by a rotating assembly having upper and lower series of cam-operated capsule-manipulating punches. Such an assembly is described in detail in U.S. Pat. No. 2,890,557, dated June 16, 1959. As described in that patent, capsules are transferred onto the rotating assembly, opened by the punches, filled with a medicinal preparation, reclosed by the punches, and swept onto a discharge chute.

To a large extent, capsules discharged from such machines have been inspected visually, and inadequately filled or otherwise defective capsules were rejected manually, there being no known way to inspect capsules and separate the good from the bad on the rapidly rotating punch assembly of the filling machine.

It is also known to transfer capsules from the rotating assembly onto a transfer disc on the periphery of which the capsules are held by a vacuum until they reach a discharge point. At the discharge point, a blast of compressed air projects the capsules away from the transfer disc toward a collection bin. Visual inspection of the capsules while on the transfer disc is also impossible because of its rapid rotation. Heretofore, automatic inspection of the capsules while on the transfer disc was considered impossible also, because the transfer disc, in order to accommodate the necessary vacuum passages, had to have a thickness such as not to permit the passage of an inspection beam transversely through a capsule of conventional size.

In accordance with this invention, elongated capsules, temporarily secured to the periphery of the rotatable transporting disc with their long axes substantially parallel to the axis of rotation, are inspected by means of a light source and a photoelectric detecting means related to each other and to the disc so that the light passing from the light source to the photoelectric detecting means travels in a direction oblique with respect to the long axes of the capsules and intersects the path of travel of the capsules. Passing the light beam through the capsules in an oblique direction permits the inspection of capsules even though they are for the most part obscured by the relatively thick transfer disc.

In accordance with the preferred embodiment of this invention, both ends of each capsule are inspected photoelectrically by oblique beams, one on either side of the transfer disc. An electrical pulse generated as a result of the passage of a defective capsule past the inspection head initiates the operation of reject means at an appropriate time for effecting removal of the defective capsule from the transfer disc. Electrical circuitry is provided for insuring that a capsule is rejected if either or both ends are inadequately filled, and for counting satisfactory and unsatisfactory capsules, and for automatically stopping the capsule filling machine when the number of satisfactory capsules reaches a predetermined number.

The principal object of the invention is to permit the automatic inspection of capsules while travelling at high speed on the transfer disc of a capsule filling machine.

Other important objects include the inspection of both ends of a capsule on a transfer disc; the reliable automatic rejection of defective capsules; and the improvement of the speed of capsule production without a corresponding sacrifice in quality. Other objects will be apparent from the following detailed description when read in conjunction with the drawings.

BRIEF DESCRIPTION OF THE DRAWINGS

FIG. 4 is a vertical section of the light-source mounting member of the inspection head in accordance with the invention;

FIG. 5 is a top plan view of a capsule transfer disc, showing the relative relationships between the inspection head, the rejected capsule receiving means, and the receiving means for satisfactory capsules;

DETAILED DESCRIPTION

Figure 1:
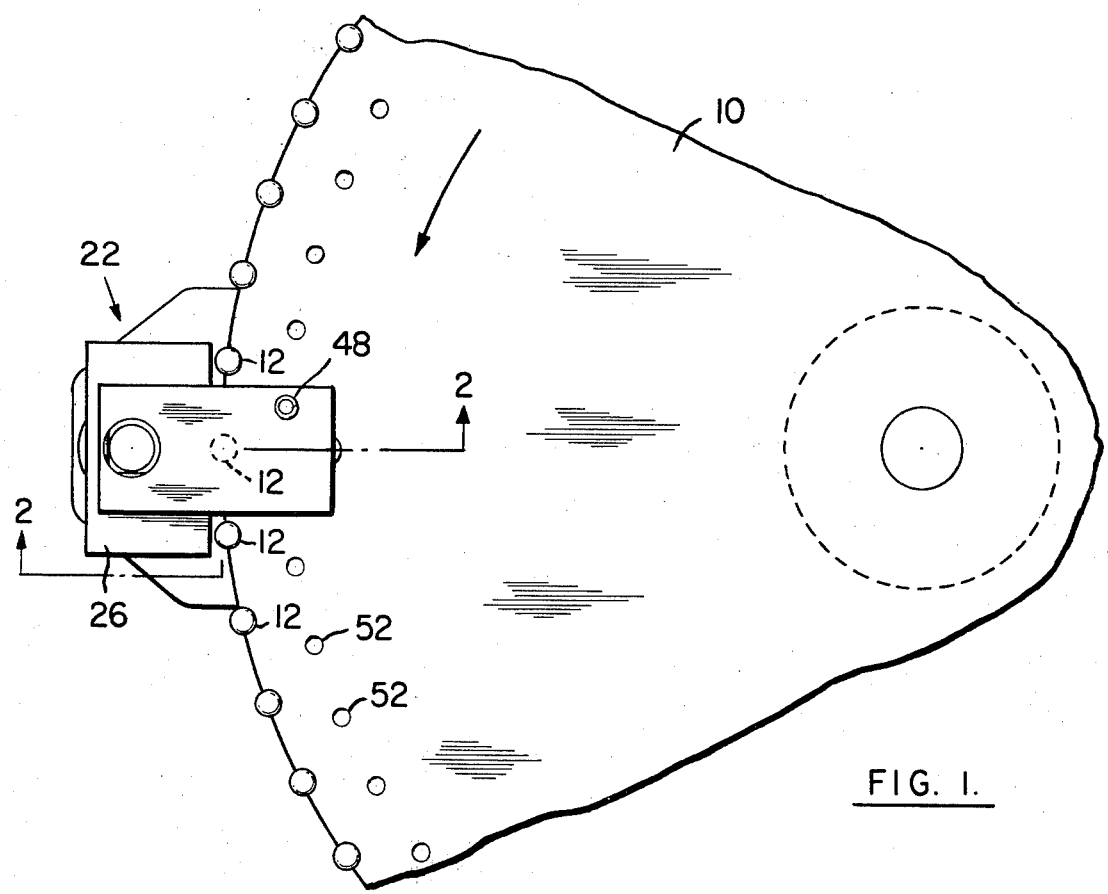
FIG. 1 is a top plan view of a fragmentary portion of a capsule transfer disc, showing its relationship with a capsule inspection head in accordance with the invention.

Referring to FIG. 1, a capsule transfer disc 10 is provided for the purpose of transporting capsules from capsule-filling apparatus to a discharge location. The capsules 12 are held in semi-cylindrical recesses in the periphery of the transfer disc by a vacuum.

Figure 2:
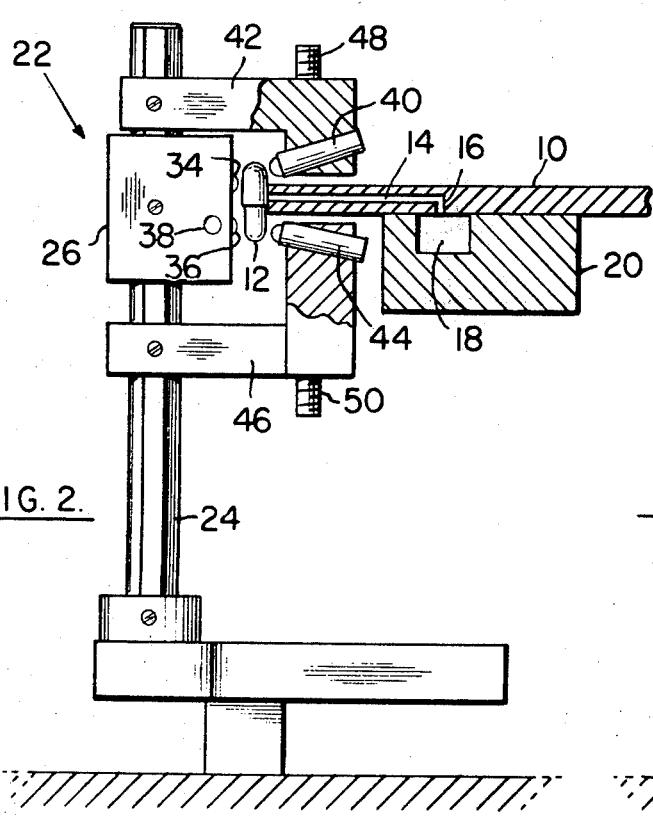
FIG. 2 is a side elevation of the capsule inspection head, as viewed from the bottom of FIG. 1, the inspection head being partially cut away to show the mountings of photoelectric detecting means, and the transfer disc being shown in vertical section to reveal one of its internal vacuum passages.

As shown in FIG. 2, the vacuum is drawn through radial passages 14 which communicate through axial passages 16 with an arcuate channel 18 provided in channel member 20. The configuration of channel 18 and member 20 is shown more clearly in FIG. 6. As is obvious from FIG. 6, the vacuum channel extends through an arc somewhat longer than half of a circle. A vacuum, for retaining the capsules on the periphery of the transfer disc 10, is thus maintained from the point at which the capsules are picked up by the transfer disc to the point at which they are discharged.

Intermediate the point at which capsules are picked up by the transfer disc, and the point at which they are discharged, there is provided an inspection head, generally indicated at 22 in FIGS. 1, 2, 3, and 5. As shown in FIG. 2, the inspection head comprises a number of elements mounted on a post 24. A light source mounting block 26 (FIGS. 2 and 4), mounted on post 24, supports a light source 28 in an oblique channel 30, channel 30 being comprised of aligned channels in the block 26 and in post 24. A second light source 32 is mounted in a horizontal passage 38 (FIG. 2). Lenses 34 and 36 on the respective light sources are arranged to project oblique beams, the beam from light source 28 being projected in an upward direction, and the beam from light source 32 being projected in a downward direction.

The light sources can be of various types. While incandescent light sources are shown, alternative light sources such as light-emitting diodes can be used as well. It will also be apparent that the two diverging beams can emanate from a single light source, if desired.

As shown in FIG. 2, a photoelectric detector 40 (a phototransistor, photodiode, or other photo-sensitive device) is mounted in bracket 42 on post 24, and arranged to receive light traveling in an oblique path from lens 34, through capsule 12. Similarly, a photoelectric detecting device 44 is provided in bracket 46 and arranged to receive a beam from lens 36, passing through the lower part of capsule 12 in an oblique direction. The oblique direction of the beams of light traveling from the light source or sources to the photoelectric detectors 40 and 44 permits the inspection of both the upper and lower parts of the capsules while they are retained in the semi-cylindrical channels of the transfer disc.

Figure 3:
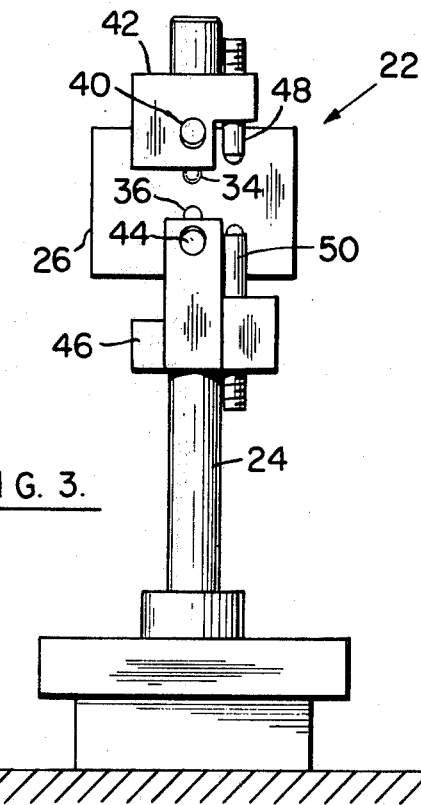
FIG. 3 is an elevation of the inspection head, as viewed from the right-hand side of FIG. 2.

As best shown in FIG. 3, a light source 48, mounted in bracket 42, is arranged to project a beam of light downwardly toward photoelectric detector 50, mounted in bracket 46. This beam is alternately blocked by the surface of the transfer disc and passed through vertical passage 52 in the transfer disc, and provides synchronization pulses which are utilized in control circuitry hereinafter described.

Figure 9:
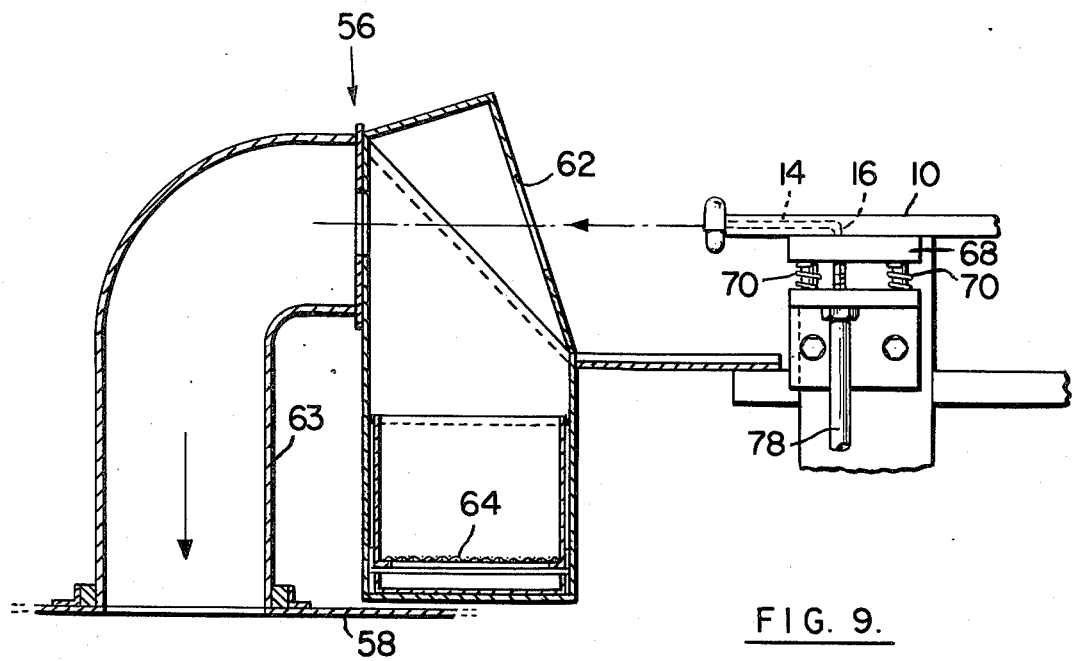
FIG. 9 is a vertical section of the satisfactory capsule receiving means.

As shown in FIG. 5, capsules, picked up by the transfer disc 10 from the filling apparatus 54 are transported in a counterclockwise direction, past the inspection head 22, to a normal discharge point where capsules are ejected from the disc into a receiver 56, which delivers the capsules into a drum 58 (FIG. 9). Between the receiver 56 and the inspection head, there is provided a receiver 60 for defective capsules, which are discharged at a location preceding the location at which satisfactory capsules are discharged into receiver 56.

Figure 6:
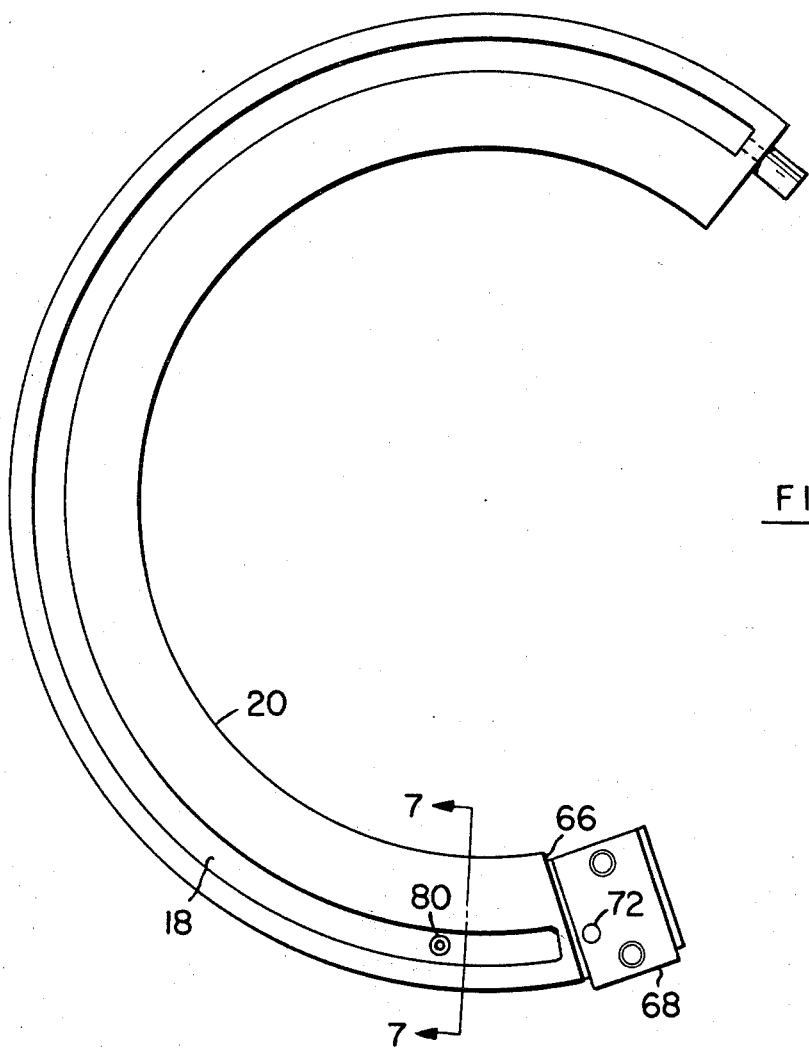
FIG. 6 is a top plan view of the vacuum channel located underneath the transfer disc together with the air nozzles provided for pneumatically removing rejected and satisfactory capsules from the transfer disc at different locations.
Figure 8:
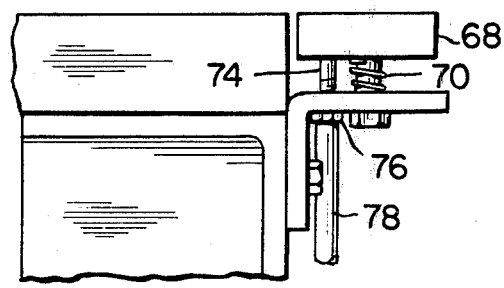
FIG. 8 is an elevation of the air nozzle for removing satisfactory capsules from the disc.

The manner in which capsules are discharged will be best understood from reference to FIGS. 6, 8 and 9, which illustrate the mechanism for discharging satisfactory capsules into receiver 56. Capsules discharged from disc 10 are projected through an opening 62, and normally enter drum 58 through channel 63. Sometimes, capsules fly apart upon discharge, and the parts of the capsule and its contents, not having sufficient momentum to enter channel 63, are caught by screen 64.

Referring to FIG. 6, at the end 66 of channel member 20, there is provided a block 68, which is urged upwardly by springs 70 (FIG. 9) against the bottom of the transfer disc 10. A vertical passage 72 in block 68 is aligned with channel 18. As shown in FIG. 9, axial passages 16 in the transfer disc come into registry with the upper opening of vertical passage 72, after they clear the end of vacuum channel 18. As shown in FIG. 8, a tubular extension 74 of fitting 76 extends upwardly into passage 72 through the bottom of block 68. Extension 74 is slidable in passage 72, permitting vertical movement of the block 68 for a tight fit against the bottom of the transfer disc. During the operation of the apparatus, air is delivered continuously through tube 78, extension 74 and passage 72, so that when an axial passage 16 comes into registry with the opening of passage 72, a blast of air is delivered through axial passage 16, and through radial passage 14 to discharge a capsule from the corresponding semi-cylindrical recess, and project it into receiver 56. Normally, this is what occurs.

Figure 7:
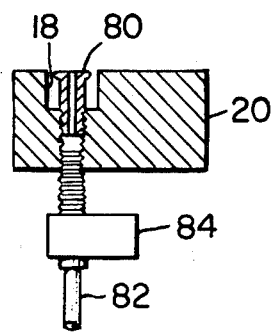
FIG. 7 is a vertical section of the reject nozzle, taken on the plane 7—7 of FIG. 6.

Defective capsules are discharged by the apparatus indicated in FIG. 7, wherein a threaded tubular element 80, having its upper end flush with the upper surface of member 20 receives air from supply line 82 through a solenoid-operated valve 84. Tubular member 80 is located in channel 18, at the position shown in FIG. 6, and it will be apparent that release of air through the passage in element 80 by the operation of solenoid valve 84, at the proper times, will effect premature discharge of defective capsules into receiver 60.

The discharge mechanism just described is operated by the actuation of solenoid valve 84 in response to signals from inspection head 22 by means of electrical circuitry which will now be described with reference to FIGS. 10 and 11.

Figure 11:
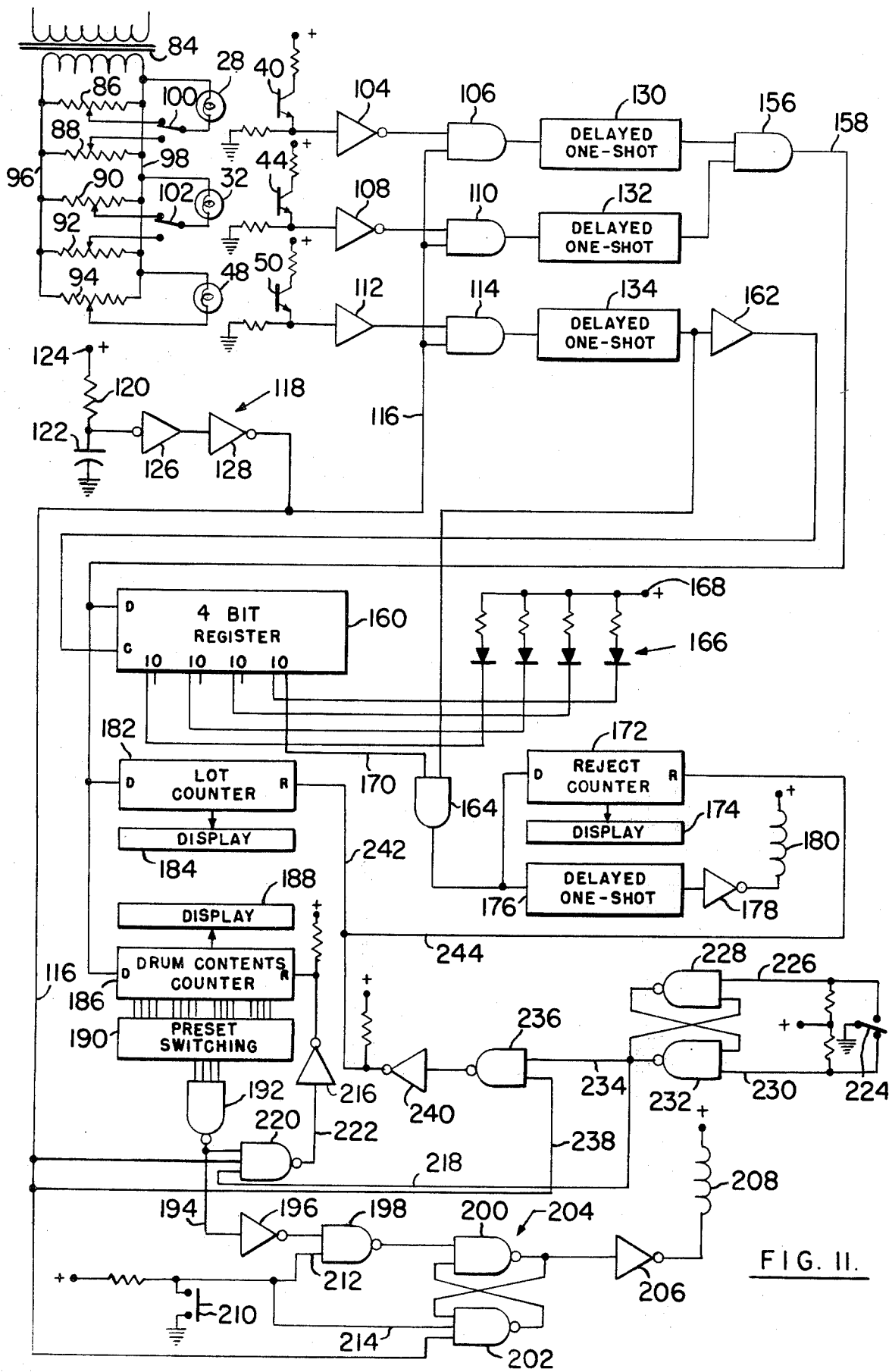
FIG. 11 is a schematic diagram of electrical circuitry used in conjunction with the inspection head of FIGS. 1–5.

In FIG. 11, a step-down transformer 84 delivers alternating current to the resistive elements of variable resistors 86, 88, 90, 92 and 94, all connected in parallel between lines 96 and 98. Light source 28 is alternatively connectable, through switch 100 to the wipers of variable resistors 86 and 88. Light source 32 is similarly connectable by switch 102, alternatively to the wipers of variable resistors 90 and 92. Light source 48 is connected to the wiper of variable resistor 94. The return for all of the light sources is through line 98. The purpose of switches 100 and 102 is to permit the light sources in the inspection head to be readily switched between two preset intensities in order to accommodate two types of capsules having different light transmission qualities. Variable resistors 86, 88, 90 and 92 may be preset accordingly.

Photoelectric detectors 40, 44 and 50, shown as phototransistors, are connected in the conventional manner, as shown, to produce positive-going signals at their emitters, when light is applied. The output of detector 40 is amplified by inverting amplifier 104, and applied to one input of a two-input AND gate 106. The output of detector 44 is similarly amplified by inverting amplifier 108, whose output is applied to one input of a second two-input AND gate 110. The output of detector 50 is amplified by amplifier 112, whose output is connected to an input of a two-input AND gate 114. The second inputs of AND gates 106, 110 and 114 are connected in common to line 116, which receives output of an "initial reset" circuit generally indicated at 118. The purpose of the initial reset circuit is to delay the enabling of the various gates momentarily as operating power is applied to the circuit so that transients inherent in the application of power do not affect the gating and counting circuits. Initial reset circuit 118 comprises a resistor 120 and a capacitor 122 connected in series between the positive DC supply, at terminal 124, and ground. The junction of the resistor and capacitor is connected through two inverting amplifiers 126 and 128 to line 116. Because capacitor 122 takes a short amount of time to charge when power is applied to terminal 124, line 116 does not go positive until a short time (eg. a half second) after power is applied.

The outputs of AND gates 106, 110 and 114 are respectively connected to the inputs of delayed one-shot multivibrators 130, 132 and 134. A delayed one-shot multivibrator is a series combination of two conventional monostable multivibrators, as shown in FIG. 10. Referring to FIG. 10, a first monostable multivibrator 136 has its "zero" output connected to the input of a second monostable multivibrator 138. The output of monostable multivibrator 138 is taken at its "one" output. Operating power for both multivibrators is derived from positive supply terminal 140 through lines 142 and 144 respectively. Capacitors 146 and 148 are the capacitors which conventionally perform the timing and coupling function in a monostable multivibrator. The timing is adjustable, in each case by adjustment of a variable resistor. For example, the timing of multivibrator 136 is controlled by the adjustment of variable resistor 150, which is connected in series with resistor 152 between the positive supply and capacitor 146. A similar timing circuit is provided in association with multivibrator 138. The operation of the circuit in FIG. 10 is such that when a positive-going pulse is applied to the input line 154, a first interval is initiated, during which monostable multivibrator 136 shifts to its unstable state. At the end of the first interval, the "zero" output of monostable multivibrator 136 goes positive, and triggers monostable multivibrator 138. The "one" output of monostable multivibrator 138 goes positive for a second interval. In other words, each time a pulse is applied to the input of the delayed one-shot, after a short delay, there appears a pulse of predetermined duration at its output.

Returning to FIG. 11, the pulses at the outputs of delayed one-shots 130 and 132 are delivered to the two inputs of a two-input AND gate 156, which delivers a positive-going pulse to line 158 if there is coincidence between the outputs of delayed one-shots 130 and 132. Thus, a positive-going pulse appears in line 158 for each satisfactory capsule which passes the inspection head. If either the upper part or the lower part of the capsule is not filled, the pulse in line 158 is not produced. Line 158 leads to the data input of a conventional four bit shift register 160.

Each time the beam from light source 48 passes through one of the axial openings in the transfer disc and strikes photoelectric detector 50, a pulse is produced which triggers delayed one-shot 134. The output of delayed one-shot 134 is delivered through amplifier 162 to the clock input of shift register 160. The output of delayed one-shot 134 is also delivered to one of the inputs of a two-input AND gate 164. So long as the data input is high when a clock pulse appears at the clock input of shift register 160, no change takes place in the conditions of the "one" and "zero" outputs. The "one" outputs are normally high, and the "zero" outputs are normally low. Each of the "one" outputs is connected to one of a series of four light-emitting diodes 166, which are connected through resistors to positive supply terminal 168. The light emitting diodes indicate the condition of the shift register, and they become illuminated whenever their corresponding "one" shift register outputs go to a low condition. The "zero" output of the last stage of shift register 160 is connected through line 170 to the other input of AND gate 164. The output of AND gate 164 is connected to the data input of a reject counter 172, which is provided with a display 174, for indicating the number of unsatisfactory capsules which pass the inspection head. The output of AND gate 164 is also connected to the input of a delayed one-shot 176, the output of which is amplified by amplifier 178 and connected to solenoid 180, which is the solenoid operating solenoid valve 84.

Whenever an unsatisfactory capsule passes the inspection head, the shift register 160 produces a high output in line 170 after a delay. When line 170 is high, and a clock pulse appears at the output of delayed one-shot 134, the output of AND gate 164 triggers delayed one-shot 176, and a pulse is delivered to solenoid 180, which releases solenoid valve 84 momentarily to effect projection of the defective capsule, which was detected by the inspection head, into receiver 60 (FIG. 5).

Figure 10:
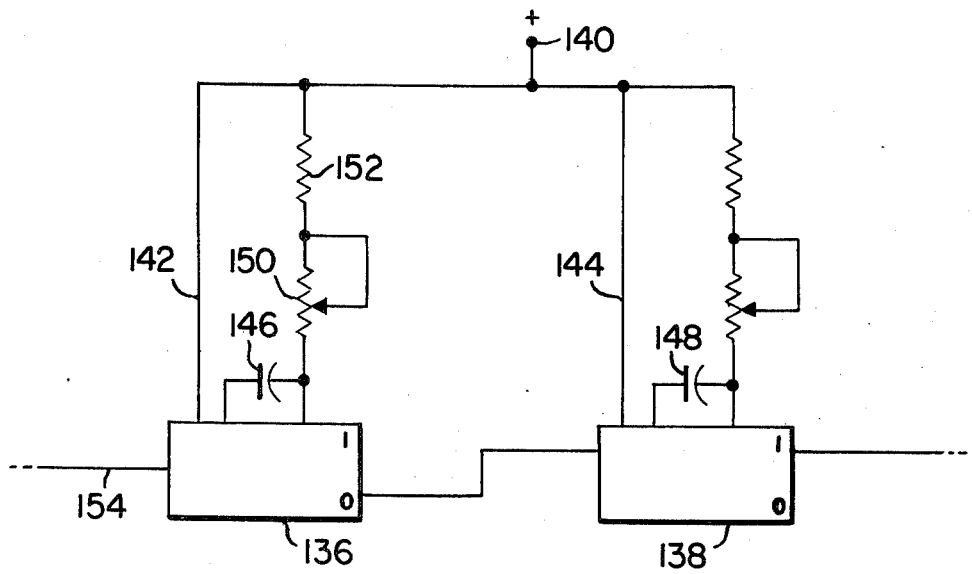
FIG. 10 is a schematic diagram of a delayed one shot of the type used in the circuitry of FIG. 11.

The adjustments provided in delayed one-shot 176 (as shown in FIG. 10) permit the timing of the blast of air which effects rejection of capsules, both in duration and in time of initiation, for optimum reliable operation.

The pulses in line 158 corresponding to satisfactory capsules are delivered to a lot counter 182, which is provided with a display 184, and also to a drum contents counter 186, which is provided with a display 188. The drum contents counter is provided with preset switching indicated at 190, so that counter 186 and preset switching 190 constitute a presetting counter. A four-input NAND gate 192 has its inputs connected to the preset switching, and produces a low in line 194 when and only when the count in counter 186 reaches the count called for by the preset switching. Preferably, the drum contents counter 186 is a six digit decade counter, and preset switching 190 is provided only for the four most significant digits. The output of NAND gate 192 is connected through inverting amplifier 196 to one input of a two-input NAND gate 198, the output of which is connected to an input of NAND gate 200. NAND gate 200, together with three-input NAND gate 202 are connected in a latch circuit 204. The output of the latch circuit, taken at the output of NAND gate 200 is delivered through inverting amplifier 206 to control solenoid 208. Control solenoid 208 controls switching which stops the capsule-filling machine when the count of drum contents counter 186 reaches the preset count.

Push-button 210 is a resetting push button, which resets latch 204 by applying a low through line 212 to one input of gate 198 and through line 214 to one input of gate 202. Momentary depression of push button 210 returns the output of inverting amplifier 206 to a high condition, deenergizing solenoid 208.

Reset terminal "R" of the drum contents counter 186 is connected to receive the output of inverting amplifier 216, the input to which is derived from three-input NAND gate 220 through line 222. One of the three-inputs of NAND gate 220 is taken from the output of NAND gate 192. Another is taken from line 116. The third is taken from line 218, which is connected to the output of a bistable latch comprising a pair of two-input NAND gates 228 and 232.

Manual resetting of drum contents counter 186, lot counter 182 and reject counter 172 is effected simultaneously by the actuation of switch 224. Switch 224 is shown in its normal position. When it is switched to its other position, input line 226 of gate 228 goes low, and input line 230 of gate 232 goes high, and the output of the latch is delivered from the output of gate 232 to lines 234 and 218. When the switch 224 is operated, lines 234 and 218 go low. Line 234 is connected to one input of a two-input NAND gate 236, the other input of which is received from initial reset line 116 through line 238. The output of gate 236 goes high upon actuation of switch 224, and is amplified by amplifier 240 and delivered through line 242 to the reset terminal of lot counter 182 and through line 244 to the reset terminal of reject counter 172. The low in line 218 is delivered to NAND gate 220, causing its output to switch to a high condition, and causing drum contents counter 186 to be reset. Drum contents counter 186 is also automatically reset, when the preset count is reached as a result of a low at the output of NAND gate 192.

The invention provides for high speed inspection and automatic rejection of capsules while traveling at high speed on a transfer disc by a unique combination of mechanism and electronic circuitry which effects discharge of rejected capsules at a location along the periphery of the transfer disc which is remote from the inspection location and spaced therefrom by a distance determined by the delay of the shift register 160 and the delay imposed by delayed one-shot 176. Importantly, the discharge position for rejected capsules is essentially independent of the speed of rotation of the transfer disc because the shift register operates on clock pulses which are produced in response to the passage of axial holes 52 in the transfer disc past light source 48 and photoelectric detection means 50. By choosing the proper number of stages in the shift register, the discharge location can be placed at any desired relationship to the inspection location without affecting the accuracy of the operation of the automatic discharge. Adjustments in the exact location of the discharge point may be made by adjustment of the variable resistor in delayed one-shot 176 corresponding to variable resistor 150 in FIG. 10.

Numerous modifications in addition to those discussed above may be made without departing from the scope of this invention as defined in the following claims.

I claim:

1. In a medicinal capsule filling machine wherein a plurality of capsules are filled with a flowable solid medicament, a rotatable disc for transporting elongated capsules temporarily secured to its periphery, means for temporarily securing capsules to the periphery of said disc in an orientation such that the long axes of the capsules are substantially parallel to the axis of rotation of the disc, inspection means comprising a light source and photoelectric detecting means both arranged adjacent to the periphery of said disc, and related to each other and to said disc so that light passes from the source to the detecting means in a straight line which is oblique with respect to the long axes of the capsules, which intersects the path of travel of the capsules, and which, if extended, will not pass through said disc, said light source and photoelectric detecting means being arranged so that the light passing from the source toward the detecting means is directed through a passing capsule near one of its ends, and said inspection means including a second photoelectric detecting means arranged adjacent the periphery of the disc and related to the light source so that light passes from the light source to the second detecting means in a straight line which is oblique to the long axes of the capsules and which intersects the path of travel of the capsules, and is directed through said passing capsule near the other of its ends in a direction such that said straight line, if extended, will not pass through said disc.

2. Apparatus according to claim 1 including means responsive to the output of both said detecting means for effecting removal of a capsule from said disc after a predetermined time if either end of the capsule is inadequately filled.

3. Apparatus according to claim 1 including means responsive to the outputs of both said detecting means for producing a coincidence pulse if and only if the capsule passing the inspection means is adequately filled at both ends, means for producing synchronization pulses substantially simultaneously with the passage of the inspection means by a capsule, shift register means having a clock input for receiving said synchronization pulses and a data input for receiving said coincidence pulse, said shift register means being responsive to the presence of a synchronization pulse at its clock input in the absence of a corresponding coincidence pulse at its data input for producing an output pulse after a predetermined number of synchronization pulses are received, and rejection means located along the periphery of the disc and separated from the inspection means by a peripheral distance, said rejection means being responsive to said output pulse for removing, from the periphery of the disc, each capsule which passes the inspection means without causing the production of a coincidence pulse.

* * * * *